United States Patent [19]

Russell

[11] Patent Number: 5,782,743

[45] Date of Patent: Jul. 21, 1998

[54] MAGNETIC MEDICAL TREATMENT DEVICE

[76] Inventor: John J. Russell, P.O. Box 752, Westbury, N.Y. 11590

[21] Appl. No.: 845,103

[22] Filed: Apr. 21, 1997

Related U.S. Application Data

[63] Continuation-in-part of Ser. No. 643,485, May 6, 1996, abandoned.

[51] Int. Cl.$^6$ ............................................. A61B 17/52
[52] U.S. Cl. ................................................ 600/9; 600/15
[58] Field of Search ............................ 600/9, 15; 128/845, 128/846, 869, 870, 876, 878, 879, 881, 882

[56] References Cited

U.S. PATENT DOCUMENTS

| | | | |
|---|---|---|---|
| 178,611 | 6/1876 | Dye | 600/15 |
| 4,621,617 | 11/1986 | Sharma | 600/16 |
| 4,840,178 | 6/1989 | Heide et al. | 600/25 |
| 5,312,321 | 5/1994 | Holcomb | 600/9 |
| 5,389,061 | 2/1995 | Nor | 600/15 |
| 5,642,739 | 7/1997 | Fareed | 600/15 |

*Primary Examiner*—Jennifer Bahr
*Assistant Examiner*—Rosiland Kearney
*Attorney, Agent, or Firm*—Nathaniel Altman

[57] ABSTRACT

A magnetic therapeutic device including a flexible elasticized loop-type fabric band or belt having a buckle loop at one end and a hook-type fastening element (VELCRO) at the other end thereof for securing the band or belt around the to-be-treated portion of a user's body, one or more magnetizable stainless steel C-shaped clips slidably mounted for adjustable positioning on the band or belt, each clip having at least one recess for magnetically holding at least one small high-intensity permanent magnet therein. The clips, which actually increase and enhance the intensity and penetration of the magnetic field emanating from the magnet or magnets, may be moved along the band or belt easily, even when already being worn, to direct the magnetic energy into the human or animal body to the area where pain alleviation or healing is required; and the number and distribution of clips or magnets on the band or belt may be increased and assembled closely for more concentrated, deeper magnetic force penetration, or reduced and spread out for milder, more gentle magneticc therapy.

9 Claims, 6 Drawing Sheets

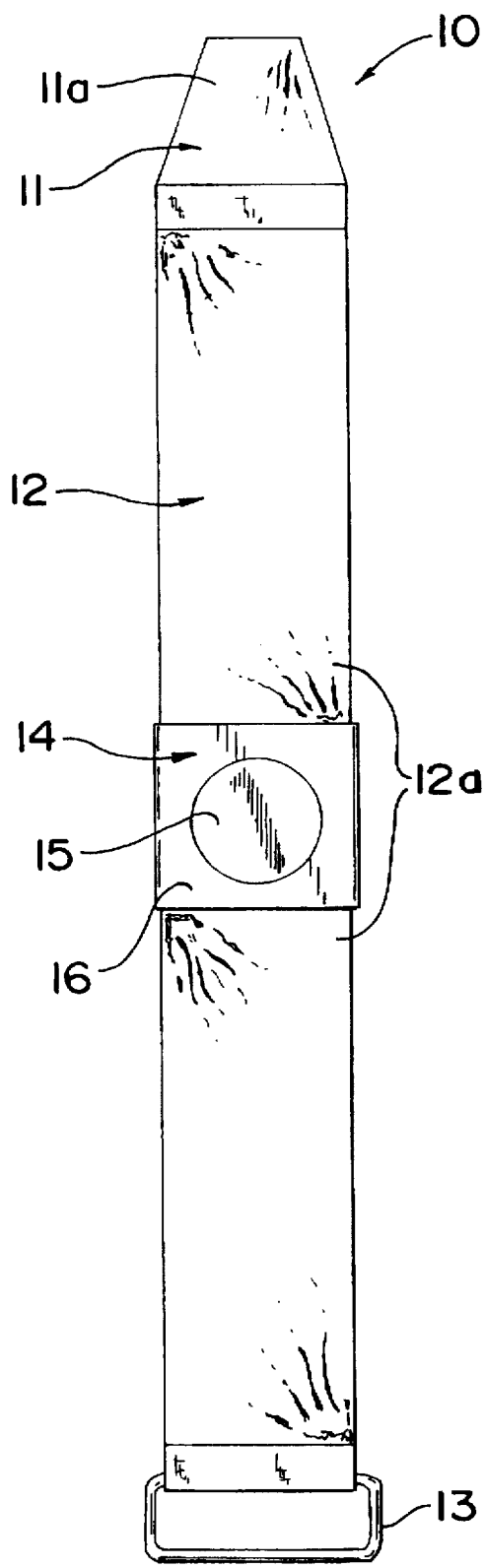
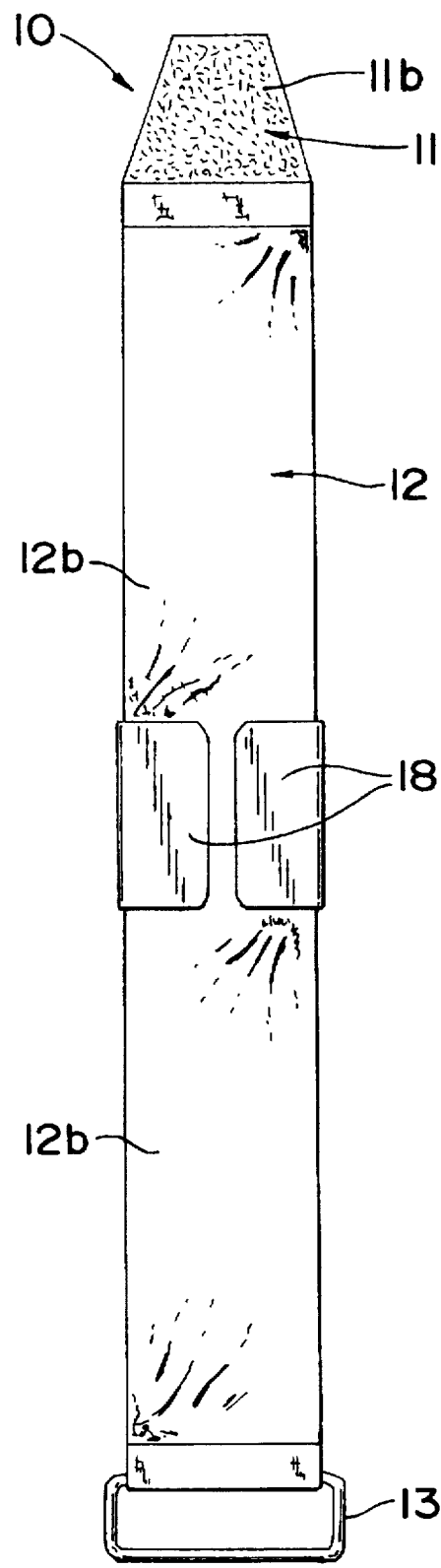

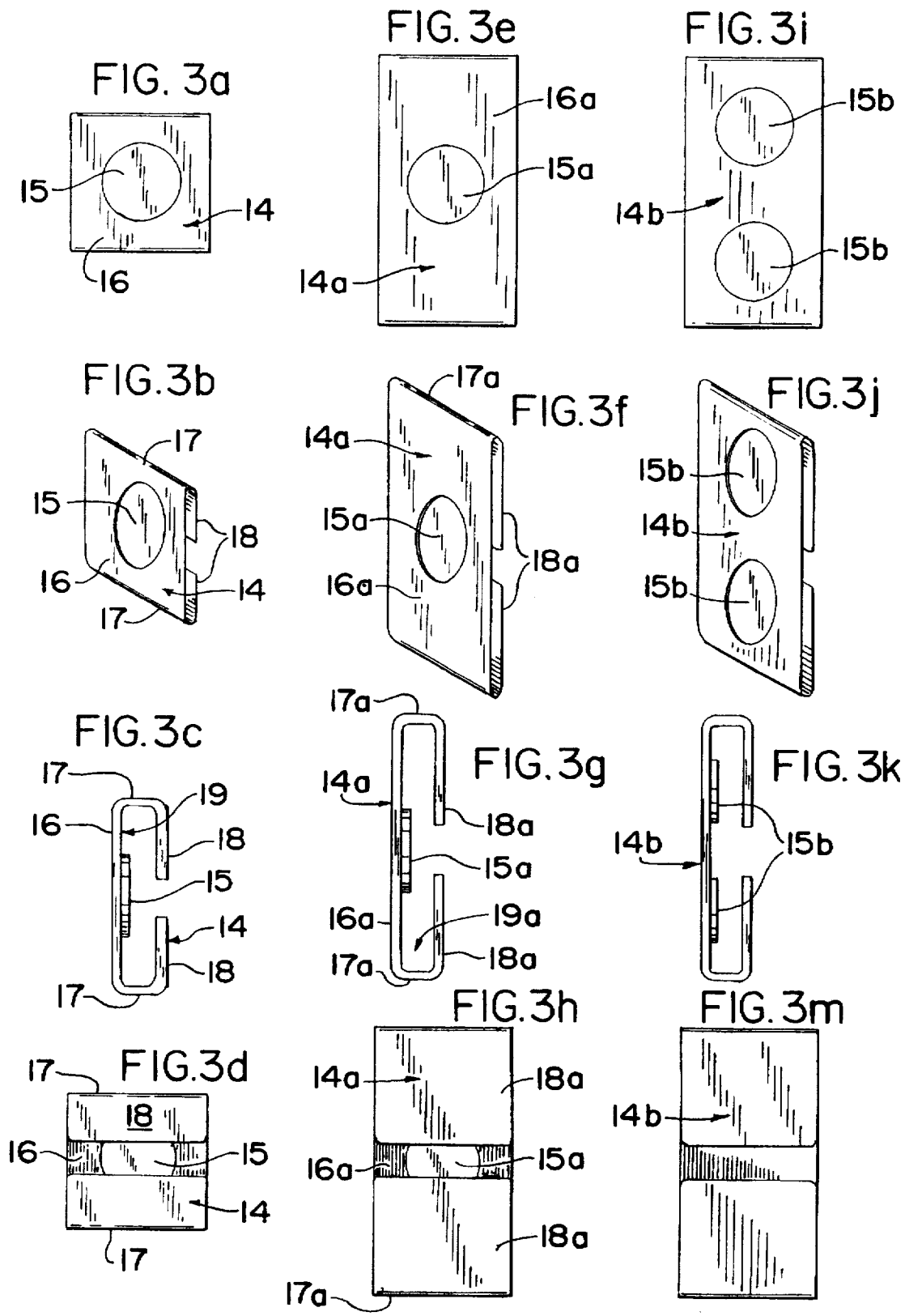

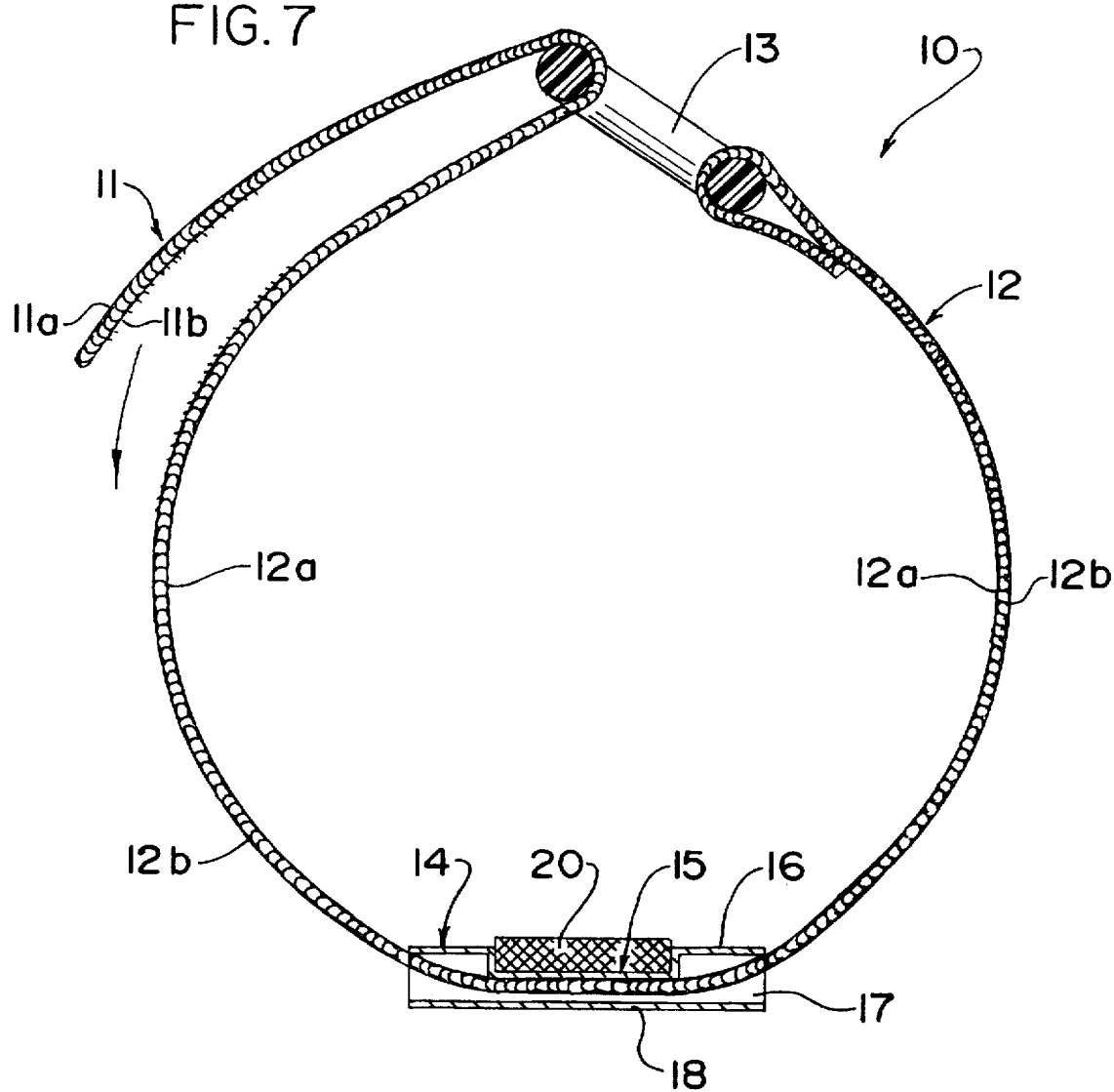

MAGNETIC MEDICAL TREATMENT DEVICE

This continuation-in-part application is based on U.S. application Ser. No. 08/643,485, filed May 6, 1996, which is now abandoned.

BACKGROUND OF THE INVENTION

A. Field of the Invention

This invention relates to devices for applying magnets adjustably to areas of the body of a user for therapeutic pain-easing and healing effects. More specifically, this invention is concerned with novel metal magnet-carrying and magnet-enhancing clips mounted slidably and adjustably on elasticized straps, bands and belts for selectively and adjustably holding powerful rare-earth magnets at or near a user's skin at painful and/or therapy-needing body regions for non-invasive treatment and symptomatic pain relief.

B. Description of the Prior Art

Magnetic treatment for healing and the reduction of pain has been used for centuries all over the world. Magnets have been known to be the most natural and economical means of treating body pains and ailments, and many methods have been used to apply magnets to ease or heal body areas and thereby to avoid the use of injections, pills, salves, or body-invasive procedures.

Clinical tests have proven that when magnets are applied to painful areas of the body, magnetic energy deeply penetrates the user's body tissue and creates a magnetic field within the body that energizes, speeds circulation of, and helps oxygenate the blood. The white corpuscles, known to be the body's healing agent, are activated and the red blood cells more rapidly oxygenated. The charged ion particles in the blood are moved about more vigorously and the moderate heat thus developed helps to increase the blood flow, ease the pain and encourage the body to perform its natural healing functions.

The field of magnetic therapy and its recent status has been explored in some detail in the following U.S. Pat. Nos. 3,921,628, issued Nov. 5, 1975 to Nakayama; 3,943,912, issued Mar. 16, 1976 to Nakayama; and 4,587,956 issued May 13, 1986 to Griffin et al. In essence, the statements in the above-cited prior art as to the effectiveness of magnetic therapy as applied to the human or animal body for easing pain and healing have been substantiated by scientists, doctors, biologists and therapists the world over and for centuries past.

References cited in the application parent to this application are: British Patent No. 1665, issued Jun. 1, 1872 to Darlow; U.S. Pat. No. 178,611, issued Jun. 13, 1876 to Dye; U.S. Pat. No. 658,027, issued Sep. 18, 1900 to Steiger; U.S. Pat. No. 4,621,617, issued to Sharma; and U.S. Pat. No. 4,840,178, issued to Heide et al. Darlow teaches a dispersion of magnetizable particles of iron, steel or oxides thereof in an adhesive binder, spreading the mixture on a fabric or leather surface and magnetizing it, then covering it with a second piece of fabric or leather and cutting the resulting laminate into smaller pieces to serve as portable magnets. Dye discloses a voltaic belt comprises a felt band to which a row of flat plates are fixedly secured by clinching them over the edges of the felt, each plate having a disk magnet with a projection ending in an eye loop extending through both its plate and the felt, the eye loops having a copper wire running therethrough to connect the magnets, all secured and supported by a protecting-band along the voltaic belt. Steiger teaches a therapeutic unit which comprises an outer thin non-magnetic metal outer ring concentrically enclosing a nearly-complete ring of magnetized steel, with a soft iron keeper filling the space between the ends of the magnet and a copper disk filling the inner cavity of the unit, the assembled unit to be suspended from the neck, strung on a tape as a girdle or carried in a pocket. Sharma discloses an artificial electromagnetic heart device which may be used on body tissue "rendered capable of being attracted to a magnet" by surgically introducing stainless steel gauze or thin plate, or injecting very fine filings inside the animal tissue. Heide et al. teaches the preferred use of a neodymium-iron magnet protected from corrosion by a biocompatible coating in a hearing-aid device for permanent installation in the middle ear.

All the prior art means for applying magnets to, and supporting magnets on, a user's body selectively have been somewhat crude, awkward, cumbersome or lacking in the magnetic strength, versatility, ease, adjustability, adaptibility, selectivity and economy provided by the devices of the present invention in accomplishing the pain-easing and healing effects on both human and animal bodies.

SUMMARY OF THE INVENTION

The present invention is a therapeutic device for applying to any selected area of the human or animal body at least one small lightweight intense-field permanent magnet. The device comprises at least one novel magnetizable stainless steel clip on which at least one such magnet is magnetically held in a recess therein, the at least one clip being mounted slidably and adjustably on an elasticized band, strap or belt to be adjustably fastened around the part of the user's body to be treated, positioning the at least one magnet selectively at or near the area requiring treatment. The preferred clips of this invention are formed from highly magnetizable surgical stainless steel, and cooperate with the magnets mounted thereon synergistically to provide enhancement and intensification of the strength and depth of penetration of the flux field emanating from those magnets. More than one magnet may be mounted on each clip, and multiple clips may be positioned slidably and adjustably on a single strap, band or belt either aligned in close proximity together, to increase the intensity and depth of penetration of the magnetic flux field and the energy, including moderate warming, to be applied to a specific body area, or spread apart to moderate the flux field's magnetic strength at any one point and to spread the moderated but effective treatment over a broader body area.

It is a primary object of this invention to provide therapeautic magnets, small in size and mass, yet having the highest-intensity magnetic fields, held on magnetizable clips slidably positioned on elasticized bands or belts for adjustably locating and holding the magnets and clips at or near a to-be-treated body area. Another important object of the invention is to provide the user with an easy-handling non-bulky, comfortably-fitting, non-toxic, non-irritating and non-invasive therapeutic device which offers high versatility, adjustability, reliable uniformity, comfort and convenience in its use.

Full details of the structures, features and uses of the preferred embodiments of this invention will be described in connection with the accompanying illustrative drawings, wherein:

BRIEF DESCRIPTION OF THE DRAWINGS

FIG. 1a is a top plan view of one of the stainless steel clips of this invention mounted slidably on an elasticized fabric band or belt;

FIG. 1b is a bottom plan view of the clip and belt of FIG. 1a;

FIG. 2b is a front perspective view of the assembly of FIG. 2a;

FIGS. 3a, 3b, 3c and 3d are, respectively, front elevational, right isometric, side elevational and rear elevational views of a metal clip of this invention dimensioned to be mounted slidably on a one-inch-wide elasticized fabric band;

FIGS. 3e, 3f, 3g and 3h are, respectively, front elevational, right isometric, side elevational and rear elevational views of a metal clip having a single magnet socket, the clip being dimensioned to be mounted slidably on a two-inch-wide elasticized fabric belt;

FIGS. 3i, 3j, 3k, and 3m are, respectively, front elevational, right isometric, side elevational and rear elevational views of a metal clip having two magnet sockets, the clip being dimensioned to be mounted slidably on a two-inch-wide elasticized belt;

FIG. 7 is sectional view taken through a magnetic treatment device in the process of being positioned and fastened in place.

DESCRIPTION OF THE PREFERRED EMBODIMENTS

Figure 2A:
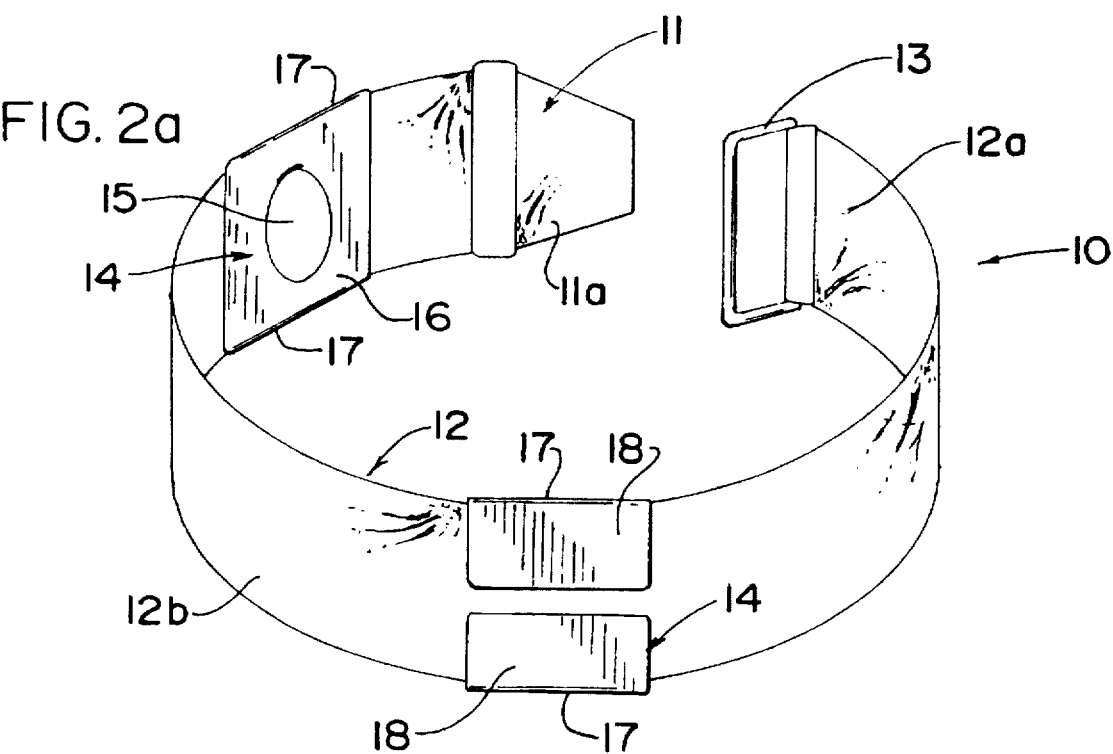
FIG. 2a is a rear perspective view of the band or belt of FIG. 1a with two stainless steel clips slidably mounted thereon.
Figure 2B:
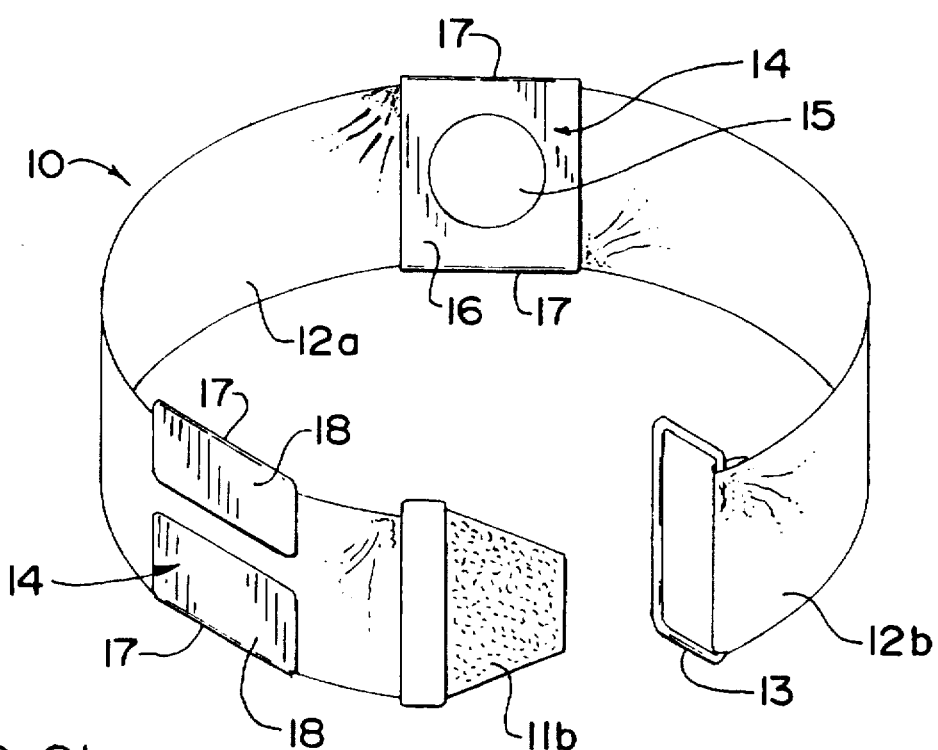

FIGS. 1a and 1b illustrate magnet-supporting assembly 10, comprising elasticized fabric band or belt 12 having fastening element 11 secured at one end and generally rectangular rigid buckle loop 13 rotatably mounted at the other end thereof. Buckle loop 13 is preferably made of non-magnetic polymeric material. Band or belt 12 is formed of a two-faced elasticized fabric, having face 12a shown in FIG. 1a of woven, smooth fabric and opposite face 12b of soft looped fabric; analogously, the FIG. 1a side 11a of fastening element 11 is smooth, while its opposite face 11b in FIG. 2 has rigid projecting hooks extending therefrom for fastening to the loops of fabric face 12b. The combination of elements 11 and 12 used here constitute a version of the hook-and-loop type fastening means available and sold under the trademark VELCRO. Band 12 as shown here has a width of one inch. Assembly 10 also includes magnetizable stainless steel clip 14 slidably and adjustably mounted on band 12. As best seen in FIGS. 3b and 3c, each clip 14 has a generally C-shaped configuration and a centrally disposed recess or socket 15 on its face dimensioned to receive fittingly one of the magnets of this invention hereinafter described. In FIGS. 2a and 2b, assembly 10 is shown with two magnetizable stainless steel clips 14 mounted slidably and adjustably on band 12, which appears in position to be placed on a portion of a user's body.

Clip 14 is more clearly seen in FIGS. 3a–3d, planar recess 15 being centered on front planar panel 16 and clip 14 extending through top and bottom bends 17 to back planar panels 18 parallel to panel 16, thus creating channel 19 for accommodating band 12 and forming the generally C-shaped configuration of FIG. 3c. Similar clip 14a shown in FIGS. 3e–3h has magnet-retaining recess or socket 15a centrally disposed on front panel 16a, top and bottom bends 17a, back panels 18a and channel 19a, and is identical in function to clip 14, but is proportioned to be mounted on two-inch-wide elasticized VELCRO belt 12a; and clip 14b, seen in FIGS. 3a–3k, 3m and 4a, differs from clip 14a only in that two magnet-receiving recesses 15b are symmetrically positioned thereon. All the clips described above are preferably made of highly-magnetizable surgical quality stainless steel, so that they are not only non-toxic and non-irritating to a user's skin but also enhance and increase the strength and depth of penetration of the magnetic flux field of any magnet or magnets held thereon magnetically. The synergistic effect of combining magnets with these highly magnetic stainless steel clips is clearly established by significantly higher magnetometer readings for the combination than for the same magnets alone.

Figure 4A:
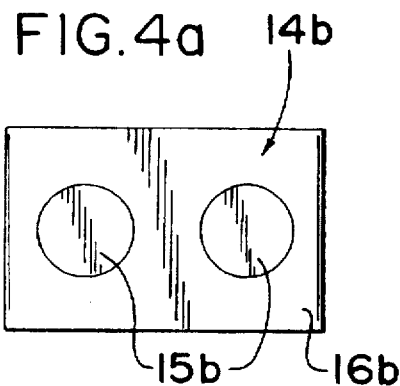
FIG. 4a is a front elevational view of the metal clip shown in FIG. 3i.
Figure 4D:
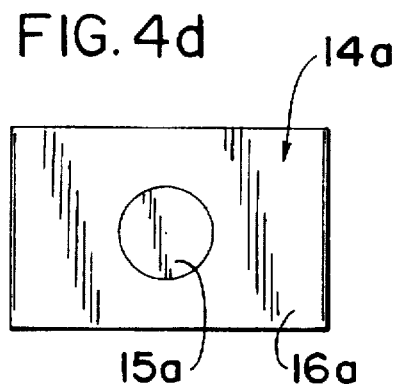
FIG. 4d is a front elevational view of the metal clip shown in FIG. 3e.
Figure 4B:
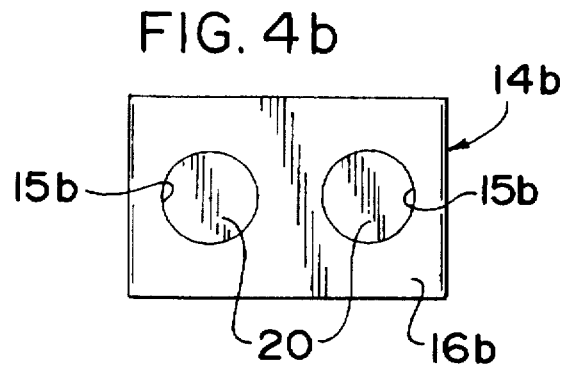
FIG. 4b is a front elevational view similar to FIG. 4a, but with two magnets positioned thereon.
Figure 4E:
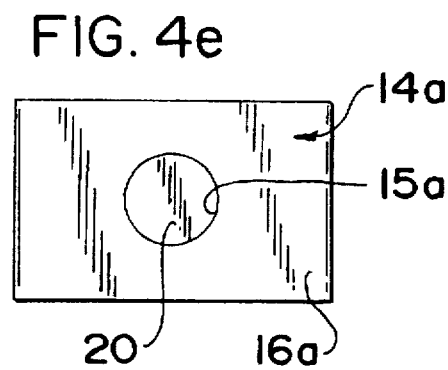
FIG. 4e is an embodiment with a single magnet.
Figure 4C:
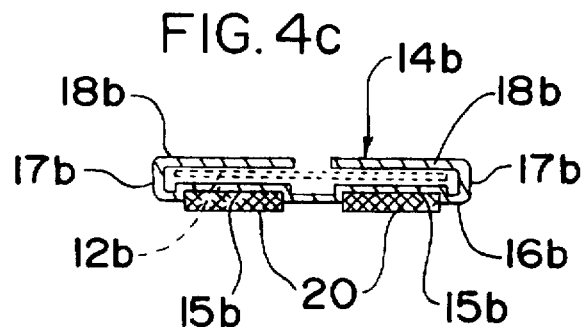
FIG. 4c is a top plan view of FIG. 4b, with the belt on which the metal clip and magnets are to be mounted shown in phantom section.
Figure 4F:
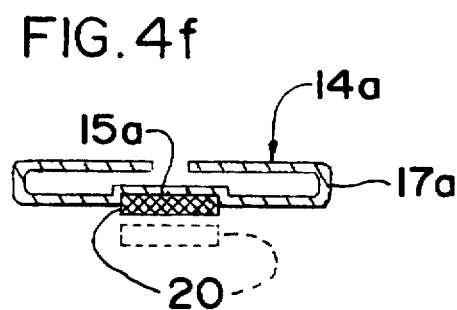
FIG. 4f is an embodiment with two additional magnets stacked on the first magnet.

FIGS. 4b and 4c show a pair of magnets 20 held magnetically in recesses 15b on face 16b of clip 14b; also seen in phantom lines in FIG. 4c is belt 12b, which, when this embodiment of the invention is assembled, passes through slot or channel 19b defined by front face 16b, bends 17b and panels 18b to hold clip 14b slidably thereon. Clip 14a in FIGS. 4d–4f has a single recess 15a which, in FIG. 4e, has a single magnet 20 held magnetically therein, while FIG. 4f shows two additional magnets 20 in phantom stacked on the first magnet 20 and held together by magnetic forces. This illustrates a method of increasing and concentrating the strength and intensity of the magnetic field to be applied to a selected area of a user's body when the therapeutic devices of this invention are used. When magnets 20 are positioned on clips 14–14b unstacked, recesses 15–15b allow the exposed magnet faces to protrude only slightly above the level of front panels 16–16b of clips 14–14b, so that both magnets and clips are in full contact with the user to ensure full advantage to a user of the increased energy emanating from the combination thereof.

Permanent magnets 20, as seen in FIGS. 4b, 4c, 4e, 4f and 6, are preferably made from rare-earth elements; they are lightweight, small, flat, cylindrical and have intense-field magnetic energy very high in comparison to other types of magnetic materials of comparable size. The most desirable rare-earth magnets now available are composed of a combination of neodymium and iron boron ferrite; their high strength/size ratio, coupled with the compact, convenient versatile clips 14, 14a, 14b ensure that the therapeutic devices of this invention are neither bulky nor awkward, but are comfortable and unobtrusive to wear. It may be noted that other shapes of magnets 20, with correspondingly-shaped recesses, such as elliptical, ovate or polygonal may be substituted without loss of function; however, flat surfaces and rounded corners of the magnets are desirable for the therapeutic device's compactness, convenience and comfort of a user As may be seen in FIG. 6, rare-earth permanent magnets 20 used in the practice of this invention are plated with gold layer 21 and outer clear plastic sheath or coating 22 to ensure that the skin of the device's user is not subjected to irritation or toxicity, and that corrosion of magnets 20 is avoided. In addition, each magnet 20 carries mark 23, in the form of an indentation and/or a color spot indicating the south pole on one side, the smooth gold opposite side being the north pole thereof. The question of the best magnetic polarity to use in therapeutic applications has not yet been resolved; experts appear to disagree on whether exposure to north, south or alternating magnetic flux fields provides optimum results. The devices of this invention make it possible for each user to determine which polar orientation suits him best; with mark 23 on each magnet as a guide, the magnets may be easily reversed on clips 14, 14a and 14b to direct the selected opposite polarity magnetic force into the user's body.

Figures 5, 6:
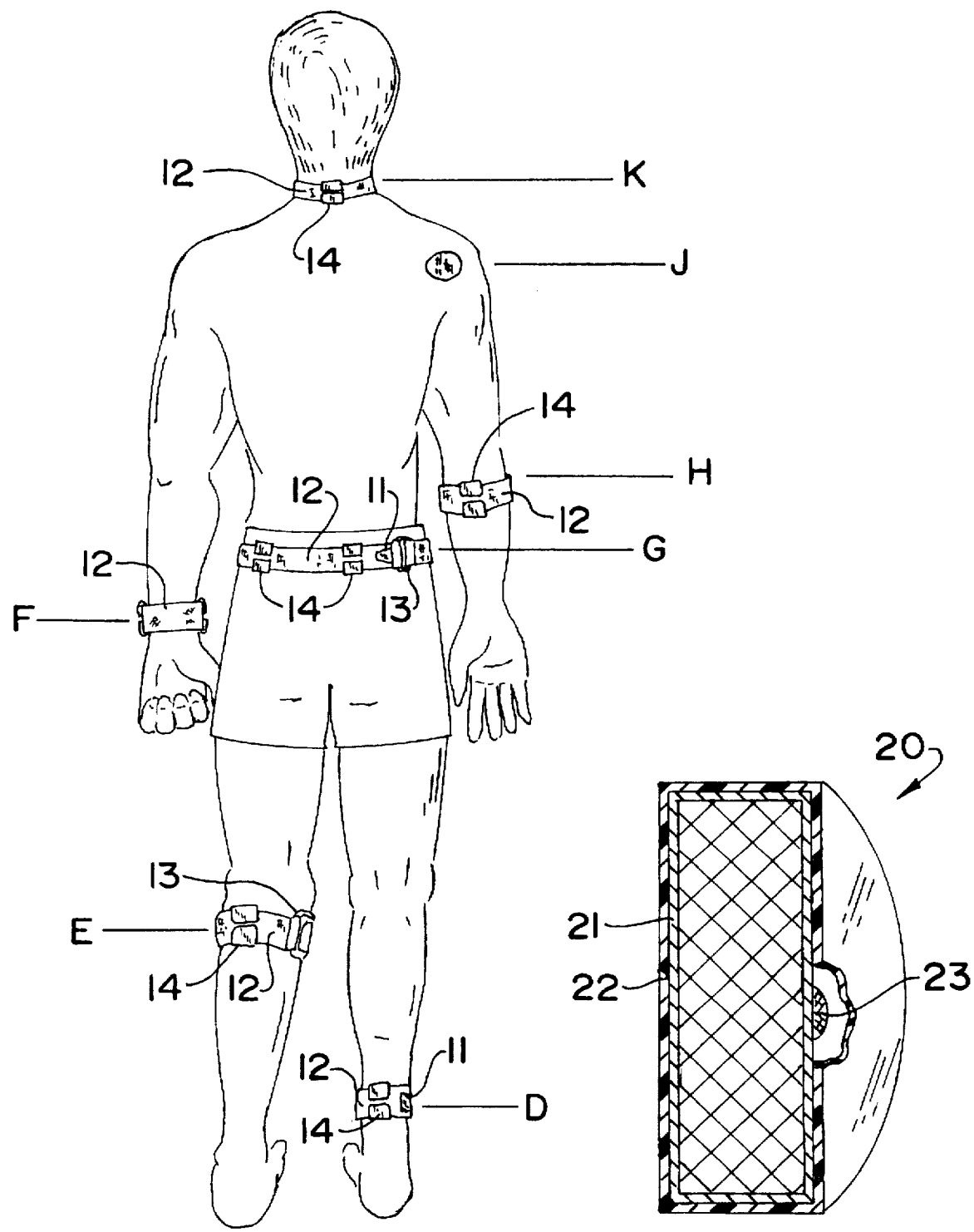
FIG. 5 is a rear elevational view of a human wearing the therapeutic devices of this invention on various portions of his body.
FIG. 6 is an enlarged sectional view taken vertically through an isometrically positioned magnet of this invention.

FIG. 5 depicts a user wearing various therapeutic devices of this invention positioned on those areas of the body most often affected by arthritis or subject to pain. The device at D provides magnetic treatment for the ankle and foot; at E, for the knee; at F, for the wrist; at G,for the back and hips; at H, for the arm and elbow; at J, for the shoulder (the magnet-carrying clip is taped in place); and at K, for the neck region. It will be clear that the therapeutic devices of this invention may be varied in length and width to be used fittingly, effectively and conveniently on many parts of a user's body, including some not shown in FIG. 5, such as the thigh, or even as a headband.

The therapeutic devices herein described, comprising novel stainless steel clips holding recessed rare-earth magnets and slidably and adjustably positioned on flexible stretchable fabric bands, belts or straps are simple to apply and completely user-adjustable with respect to the number and distribution of clips and magnets at or near the body area being treated. As best seen in FIG. 7, band or belt 12 is secured around the body part being treated by having passed hook fastening element 11 through buckle loop 13, pulled elasticized band 12 to comfortable tightness and pressed element 11 against outwardly-facing loop-fabric surface 12b for latching attachment. Prior to closing band 12, magnet-carrying clip or clips 14, 14a or 14b have been added and slidably positioned on band 12 either closely together, possibly with more magnets added (see FIG. 4f) for stronger more intense magnetic energy penetration into a specific body area; or clips 14, 14a and 14b may be spread apart and reduced in number to moderate the applied magnetic field and to provide treatment to a broader body region. It is also contemplated that the assortment of clips 14, 14a and 14b, made from differing stainless steel compositions with varying magnetic susceptibilities and suitably distinguished from each other by indicia, may be provided, perhaps as a kit, so that the user may adjust the magnetic intensity of any treatment by clip selection as well as by the number and spacing of magnets.

While the therapeutic devices of this invention are non-toxic, non-irritating and primarily intended to be worn directly against the skin for maximum effectiveness, they may be used beneficially as well over undergarments and clothing. It may also be noted that the magnet-carrying clips 14, 14a and 14b may be readily removed by sliding yhemm from bands or belts 12, which may then be laundered and dried, avoiding damage to magnets and clips, before reassembling each therapeutic device by replacing clips and magnets on each band or belt.

The preferred embodiments and best modes of practicing this invention now contemplated have been disclosed. It will be evident to those skilled in the art that alterations, modifications and substitutions to the embodiments herein described may be made without departing from the concepts of this invention, which are limited only by the scope of the ensuing claims, wherein:

I claim:

1. Magnetic therapeutic device for non-invasive treatment to ease pain and to promote healing in the body of a user, by directing magnetic field flux energy into a to-be-treated area of the device user's body, which comprises:

at least one compact lightweight high-intensity rare-earth permanent magnet, each said at least one magnet having its upper and lower surfaces parallel to each other and substantially planar, at least one of said surfaces being marked to indicate the magnetic polarity and to facilitate selective orientation thereof, each said at least one magnet having its peripheral shape selected from the group consisting of: circular, elliptical, ovate and polygonal;

at least one magnetizable stainless steel magnet-carrying clip, each said at least one clip being substantially C-shaped and comprising:

a planar generally rectangular front panel having a top, a bottom and at least one recess formed symmetrically therein, each said at least one recess having a planar bottom and being shaped to accommodate fittingly each said at least one magnet therein to a depth which permits a front surface of each said magnet to protrude only marginally above said front panel's surface so that said front panel's surface is substantially coplanar with said magnet's front surface, each said magnet being held in each said recess by magnetic attraction;

transversely bent areas of said clip, said bent areas extending one from the top and one from the bottom of said front panel; and two rear planar panels extending, one from each said bent area, coplanar with one another and extending toward each other and spacedly parallel to said front panel, said front and rear panels and said bent areas thereby defining a channel between said front panel and said rear panels; and stretchable elasticized belt means for holding each said at least one clip mounted fittingly, slidably and adjustably thereon through said channel in each said clip, each said recess in said belt means comprising:

a selected length of two-faced elasticized fabric, one face thereof being woven with a smooth surface to be positioned against a user's body, the opposite face thereof having a loop-type surface;

a generally rectangular non-magnetic buckle loop rotatably held and attached by a fabric loop formed at one end of said selected fabric length;

a fastening element attached to, and extending outwardly from, the end of said fabric length opposite said buckle loop, said fastening element having a surface of rigid hooks for engaging the loops of said loop-type surface of said elasticied fabric to secure said belt means fittingly around the device user's selected to-be-treated body area, whereby, each said magnet's upper surface and each said front panel of each said slidably adjustable clip being substantially coplanar by each magnet being magnetically held in each said recess, the therapeutic magnetic device provides even contact with, and the adjustale slidability of each said clip provides accurate selective positioning, to direct each said magnet's energy flux flow into the device user's selected body area, the synergistic combination of each said magnet and each said clip thereby providing enhanced non-invasive energy flow and deeper penetration of the user's body tissue than each said magnet alone can produce.

2. Magnetic therapy device as defined in claim 1, wherein said at least one rare-earth magnet is gold-plated and sheathed in a clear polymeric coating, whereby the skin of a user is protected front toxicity and irritation, and said magnet is protected from corrosion.

3. Magnetic therapy device as defined in claim 2, wherein said at least one rare-earth permanent magnet comprises neodymium and iron boron ferrite.

4. Magnetic therapy device as defined in claim 1, wherein said stretchable elasticized belt means may vary in length and width so that a therapy device may be used fittingly for treatment of a user's foot, ankle, calf, thigh, knee, wrist, elbow, upper arm, neck and head, wherein said stainless steel clips may vary in height to fit slidably and adjustably on the corresponding said belt means, and wherein the number of said recesses in each said stainless steel clip's front panel may vary in number from one to two.

5. Magnetic therapeutic device as defined in claim 1, wherein said at least one stainless steel clip is a plurality of said clips, each said clip having at least one magnet held magnetically in each said recess therein, said plurality of clips being mounted closely together on said belt means when a user's treatment requires a concencentrated, more deeply penetrating magnetic field flux, said plurality of clips being separated and spaced apart when a user's treatment requires more moderate, more widespread therapeutic treatment.

6. Magnetic therapeutic device as defined in claim 1, wherein said magnetic field flux is selectively reversible.

7. Magnetic therapeutic device as defined in claim 1, wherein each said stainless steel clip, with each said magnet retained in each, said recess therein, can be temporarily removed from said elasticized belt means by sliding each said clip off said end of said belt means carrying said fastening element, whereby said belt means can be laundered and dried before restoring each said clip to an operative position on said belt means without exposing each said clip and each said magnet to potential damage.

8. Magnetic therapeutic device as defined in claim 1, wherein said at least one magnet is a plurality of said magnets and wherein said plurality of magnets are stacked on each other in a pile and held together magnetically on said at least one magnetic clip so that a greatly intensified magnetic flux flow may be focused on one body area of a user of the therapeutic device.

9. Magnetizable stainless steel clip for use in a magnetic therapeutic device in combination with a stretchable elasticized belt and at least one flat compact lightweight intense-field rare-earth permanent magnet, each said generally C-shaped clip comprising:

a generally rectangular planar front panel, having a top, a bottom and at least one recess formed symmetrically therein, each said at least one recess having a planar bottom and being shaped and dimensioned to accommodate fittingly therein each magnet to a depth which permits a magnet's front surface to protrude only marginally above a front surface of said front panel so that said front panel's front surface and said magnet's front surface are substantially coplanar;

transversely bent areas extending one from the top and one from the bottom of said front panel; and two rear planar panels extending one from each of said bent areas parallelly to said front panel and toward each other, said front panel, said rear panels and said bent areas thereby defining a channel through which the belt is passed to mount each said magnet-carrying stainless steel clip for fitting selective slidably adjustable positioning thereon.

\* \* \* \* \*